United States Patent [19]

Matson

[11] Patent Number: 4,497,199

[45] Date of Patent: Feb. 5, 1985

[54] LIQUID CHROMATOGRAPHY

[75] Inventor: Wayne R. Matson, Ayer, Mass.

[73] Assignee: ESA, Inc., Bedford, Mass.

[21] Appl. No.: 465,786

[22] Filed: Feb. 10, 1983

Related U.S. Application Data

[62] Division of Ser. No. 241,945, Mar. 9, 1981, Pat. No. 4,413,505.

[51] Int. Cl.³ .............................................. G01N 31/06
[52] U.S. Cl. ............................. 73/61.1 C; 204/180 G; 204/411
[58] Field of Search ............... 73/61.1 C; 204/411, 204/412, 180 G; 422/70; 436/161; 210/198.2, 656

[56] References Cited

U.S. PATENT DOCUMENTS

| | | |
|---|---|---|
| 3,649,498 | 3/1972 | Pretorius et al. |
| 3,694,335 | 9/1972 | Pretorius et al. |
| 3,993,945 | 11/1976 | Warmoth et al. |
| 3,997,836 | 12/1976 | Haruki |
| 4,033,830 | 7/1977 | Fletcher .......................... 204/411 X |
| 4,199,323 | 4/1980 | Miller, Jr. et al. |
| 4,404,065 | 9/1983 | Matson .......................... 73/61.1 C X |
| 4,448,691 | 5/1984 | Davis ................................. 210/656 |

FOREIGN PATENT DOCUMENTS 0033188 1/1981 European Pat. Off.
2923050 12/1979 Fed. Rep. of Germany.

OTHER PUBLICATIONS

"Novel Exchange Chromatographic Method Using Conductimetric Detection", Authors: H. Small, T. S. Stevens, W. C. Bauman; Analytical Chemistry, vol. 47, No. 11, pp. 1801–1809, Sep. 1975

*Primary Examiner*—Jerry W. Myracle
*Assistant Examiner*—Joseph W. Roskos
*Attorney, Agent, or Firm*—Hayes, Davis & Soloway

[57] ABSTRACT

A method of analyzing a sample material by liquid chromatography is described wherein the sample is dissolved in a carrier fluid to form a mobile phase. The mobile phase is electrochemically treated to selectively remove electroactive materials therein or to change chromatographic characteristics of said materials therein prior to passing the mobile phase to a chromatography column.

7 Claims, 8 Drawing Figures

LIQUID CHROMATOGRAPHY

This application is a divisional of my copending application Ser. No. 241,945, filed Mar. 9, 1981 now U.S. Pat. No. 4,413,505 dated Nov. 8, 1983 for Improvements in Liquid Chromatography.

The present invention relates to improvements in chromatography.

Liquid chromatography is a well-known analytical technique in which a sample material is separated into its component species by dissolving the sample material in a carrier fluid to form a mobile phase which is then passed continuously through a solid phase. Generally the solid phase comprises a bed of ion exchange resins in powder or bead form, arranged in a stack or column. The various species contained in the sample material separate as a result of their different values of attraction for the various ion exchange resins in the bed to produce a so-called eluant solution which is then passed through a detection device. Classically, detection devices for liquid chromatography have been based on measurements of optical phenomena such as differences in indices of refraction or ultraviolet absorption of the various species in the chromatographic eluant.

Two prerequisites for commercial chromatography systems are: (1) sharp separation by the solid phase of the various species in the sample so that individual species will appear at different times in the eluant, i.e. the sample is resolved into its component species; and (2) convenient means of continuously and accurately detecting and analyzing the separated species in the eluant. At the current state of the art chromatographic separation generally can be achieved at a level of selectivity that is substantially more precise than the level of sensitivity of detection achieveable using classical optically based detection devices. More recently, detection devices based on electrochemical measurements have been proposed for use in connection with liquid chromatography separations. One such proposed electrochemical detection device employs a hanging drop mercury electrode suspended in the eluant solution. However, as noted in U.S. Pat. No. 3,706,381, detectors employing hanging drop mercury electrodes have not proved to be entirely satisfactory due to the considerable noise associated with the dropping mercury. It has also been proposed to employ solid electrodes for directly measuring species in an eluant solution. One such proposed device employs a test electrode in the form of a solid graphite button or a carbon or graphite paste flat plate for contacting the eluant stream from a liquid chromatography column. However, electrochemical detection devices of this type generally are able to achieve sensitivity of 100 picograms at best, and may suffer from decay of sensitivity. Also, while electrochemical detection devices employing carbon or graphite paste electrodes may function well for many applications of reverse-phase chromatography, problems can develop when nonaqueous solvents are used due to the combination of a high volume flow rate with the mechanical instability of the carbon paste matrix. In addition, the relatively high electrical resistance of nonaqueous mobile phases can limit the linear range (on the high end) of thin layer amperometric detectors due to ohmic potential losses along the thin-layer channel. Another disadvantage of known electrochemical detection devices is that such devices generally rely on measuring changes in charge transfer phenomena; thus known electrochemical detection devices generally are limited in use to detecting only those materials capable of undergoing charge transfer.

In my copending application Ser. No. 111,917, filed Jan. 14, 1980, now U.S. Pat. No. 4,404,065 issued Sept. 13, 1983, I disclose an electrochemical detection apparatus of extreme sensitivity which essentially comprises a flow-cell having at least one active testing electrode at least one reference electrode, and at least one counter electrode. Each electrode comprises a liquid impervious solid body having a bore extending therethrough with the electrode active surface located in the bore. The electrodes are arranged in a stack, electrically insulated from one another with their respective bores aligned so as to define a flow channel through which liquid to be detected can be passed. Various electrochemical responses are achieved by varying the construction, number and arrangement of electrodes in the stack, and the potentials applied to the electrodes. While the electrochemical detection apparatus of my aforesaid U.S. Pat. No. 4,404,065 overcomes many of the aforesaid problems of the prior art, problems still subsist due to interference signals from electroactive materials in the mobile phase, and/or insufficient separation of species in the chromatography column.

It is thus a primary object of the present invention to provide a novel and improved chromotography system, i.e. method and apparatus, which overcomes the aforesaid and other problems and limitations of the prior art.

In order to effect the foregoing and other objects there is provided in a chromatography apparatus an amperometric guard cell upstream of the chromatography column. The guard cell, which is designed and constructed to operate under high pressure conditions existing on the upstream side of the chromatography column may be employed to remove selected electroactive species contained in the sample whereby to reduce the background level of contaminants reaching the column, and/or to change chromatographic characteristics of selected species in the mobile phase whereby to permit chromatographic separations that might otherwise be impossible. The amperometric guard cell comprises a chemically inert dielectric body having a bore therethrough defining a flow path, and including at least one active testing electrode, at least one counter electrode, and at least one reference electrode. The electrodes are all operatively disposed, electrically insulated from one another, within the flow path.

Yet other objects of the invention will in part appear obvious and will in part appear hereinafter. The invention accordingly comprises the apparatus processing the construction, combination of elements, and arrangement of parts, and the processes comprising the several steps and relation to one or more of such steps with respect to each of the others, all of which are exemplified in the following detailed description, and the scope of the application as will be indicated in the claims.

For a fuller understanding of the nature and objects of the present invention reference should be had to the following detailed description taken in connection with the accompanying drawings wherein.

Further understanding of the features and advantages of the present invention will be had from the following detailed description of the invention which illustrates a preferred form of amperometric guard cell of the present invention in combination with a liquid chromatography separation apparatus and an electrochemical detection cell. It will be understood, however, that the amperometric guard cell of the present invention may be advantageously employed in combination with a liquid chromatography separation apparatus employing a conventional optical detection device.

Figure 1:
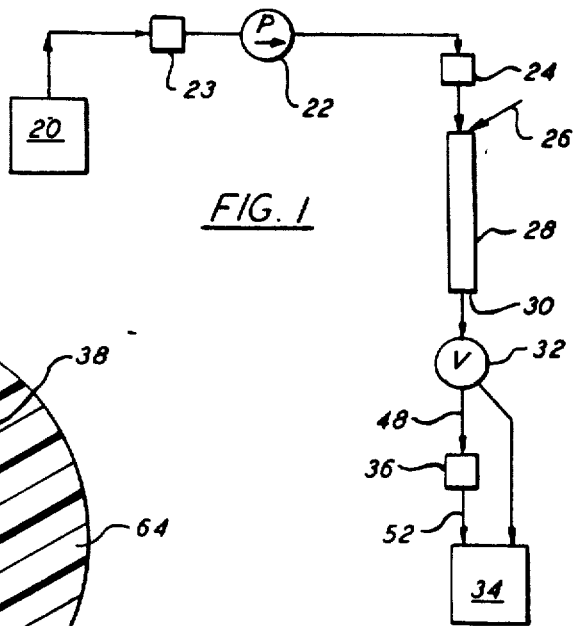
FIG. 1 is a schematic view of one form of liquid chromatography apparatus in accordance with the present invention and incorporating an amperometric guard cell in accordance with the present invention.

Referring to FIG. 1, there is illustrated a liquid chromatography apparatus made in accordance with the present invention. The illustrated liquid chromatography apparatus includes a mobile phase reservoir 20 coupled through a constant volume pump means 22, an amperometric guard cell 23 (as will be described in detail hereinafter), and an injection valve 24 and sample inlet 26 to the top of a liquid chromatography column indicated generally at 28. In practice, sample materials to be tested are introduced into the chromatography apparatus either by direct injection of microliter amounts of sample material into the chromatography column 28, e.g. through a syringe at sample inlet 26, or the sample material may be introduced into the chromatography column 28 as a dilute solution of sample material at injection valve 24. Thus, if desired, either injection valve 24 or sample inlet 26 may be omitted from the system. Chromatography column 28 is packed with selected ion exchange resins in bed or powder form. The selection of the mobile phase, and the selection and packing order of the ion exchange resins will depend on the particular separations desired and can readily be determined by one skilled in the art and thus will not be further described herein. The base of chromatography column 28 is coupled via an outlet 30 to a splitter valve 32 which divides the eluant from the chromatography column 28 between a sample collection vessel or waste container 34 and a detection device indicated generally at 36.

The illustrated chromatography apparatus (less amperometric guard cell 23) is conventional and may be of the type described by P. H. Freeman and W. L. Zielinski in U.S. Bureau of Standards Technological Note Number 589, Page 1 (July 1980 to June 1979).

Figure 3:
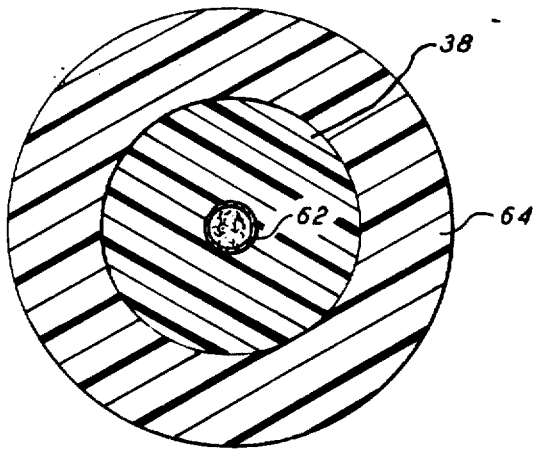
FIG. 3 is a cross sectional view of the amperometric guard cell of FIG. 2, taken along lines 3—3.
Figure 2:
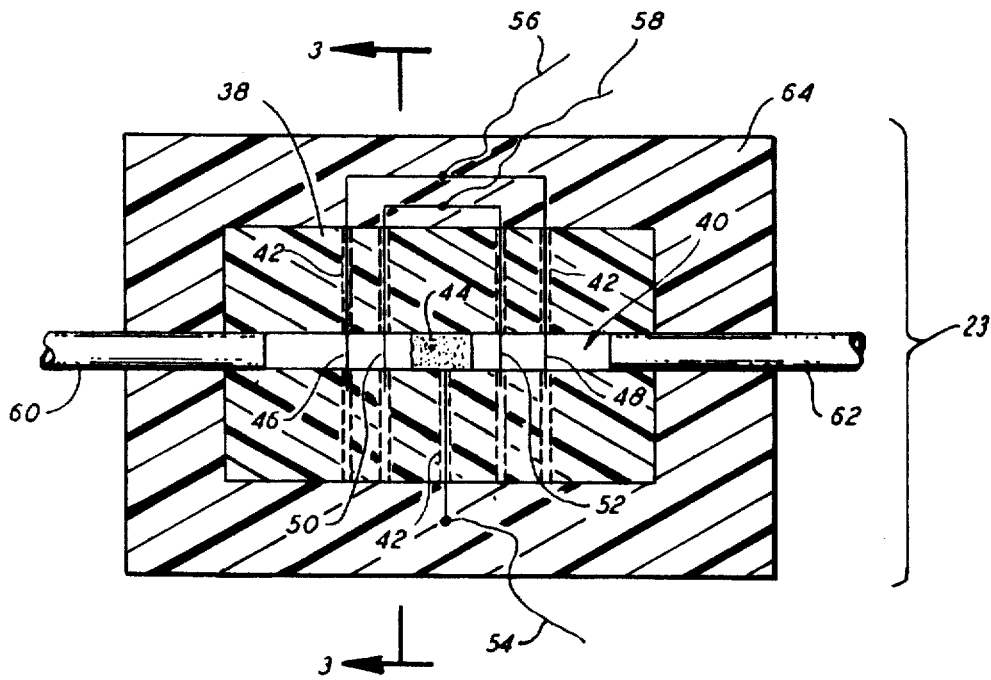
FIG. 2 is a side elevational view, partly in section, showing details of a preferred form of amperometric guard cell portion of the apparatus of FIG. 1.

Referring to FIGS. 2 and 3, amperometric guard cell 23 comprises an electrochemical flow cell indicated generally at 23 and including a hollow cylindrical body 38 formed of a rigid, liquid impervious, electrically insulating, chemically inert material such as a synthetic polymeric material, e.g. an unplasticised polyvinyl chloride, polypropylene, a polytetrafluoroethylene fluorocarbon resin such as Teflon, Kel-F, Halar, Fluoron, or other commercially available polymeric material. Cylindrical body 38 defines an elongate cylindrical flow path 40 in which are located the individual electrodes of amperometric guard cell 23, as will be described in detail hereinafter. A plurality of radial drillings or bores 42 are formed through the side wall of body 38 and provide entry for electrical connections to the electrodes located within flow path 40.

As mentioned supra, amperometric guard cell 23 has at least one working electrode, at least one reference electrode and at least one counter electrode. A preferred form of cell 23 shown in FIGS. 2 and 3 comprises five electrically discrete electrode elements arranged as follows: an active testing electrode 44, two counter electrodes 46 and 48, and two reference electrodes 50 and 52. Active testing electrode 44 comprises a short cylindrical body or fritt formed of an electrically conductive, chemical inert, porous electrode base material such as a porous metal or graphite. By nature of its porosity testing electrode 44 has a relatively high active surface area. Counter electrodes 46 and 48 also may comprise fritts of similar porous electrode base material, but preferably counter electrodes 46 and 48 comprise inert metal terminals such as one or a plurality of palladium or platinium wires. Reference electrodes 50 and 52 comprise inert metal terminals such as one or a plurality of palladium, palladium oxide or platinum wires. Preferably, reference electrodes 50 and 52 are closely spaced from and equidistant from active testing electrode 44, while counter electrodes 46 and 48 are located further away from testing electrode 44.

Active testing electrode 44, counter electrodes 46 and 48, and reference electrodes 50 and 52 are connected via palladium or platinium wires 54, 56 and 58 to sources of controlled testing potential, reference potential and working potential, respectively.

Completing guard cell 23 are a pair of rigid, high pressure resistent terminations such as stainless steel tubing segments 60 and 62. The latter are jam fitted into the respective ends of body 38 flow path 40, and body 38 in its entirety and tubing segments 60 and 62 in part, are potted or encapsulated within a high impact, chemically resistent, electrically insulating material such as an epoxy resin indicated generally 64. As seen in FIG. 2, tubing segments 60 and 62 extend beyond the epoxy potting in part to permit connection of cell 23 in line in the chromatography system. Alternatively, fittings may be molded integrally with the epoxy resin body 64, for example, as internally threaded fittings in place of tubing segments 60 and 62. Cell 23 may be placed at various points in a chromatography system as will be described in detail hereinbelow.

FIG. 1 shows the placement of a guard cell 23 upstream of injection valve 24. With cell 23 located at this position in a chromatography system, it can, through appropriate application of electrical potential to the cell, act as a screen to remove selected electroactive materials in the mobile phase used to elute column 28, thus reducing background level of contaminants reaching the column and eluting from the column. This in turn may reduce background signals and thus enhance operation of the downstream detector device 36 and/or permit the use of certain mobile phase combinations with UV or fluorescent detectors which ordinarily could not be used with such detectors. Removal of certain contaminants also may increase column life.

Figure 4:
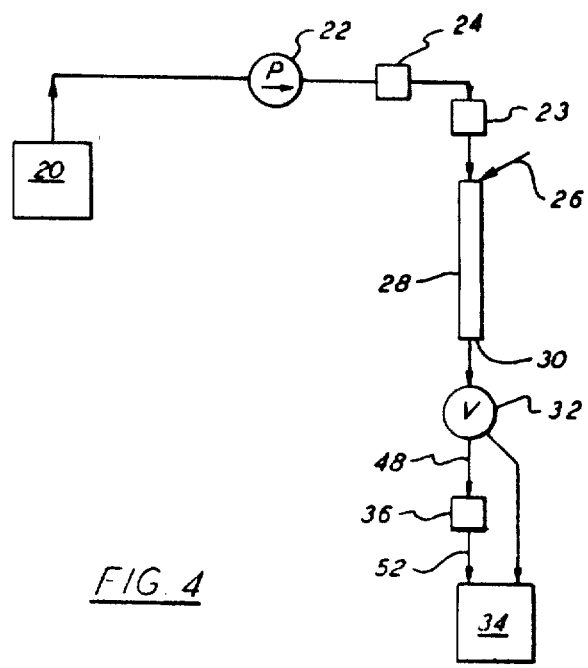
FIG. 4 is a schematic view of an alternative liquid chromatography apparatus employing an amperometric guard cell in accordance with the present invention.

FIG. 4 illustrates the placement of a guard cell 23 immediately downstream of injection valve 24. With cell 23 located at this position in a chromatography system, it can, through appropriate application of electrical potential to the cell, electrochemically modify (i.e. oxidize or reduce) selected materials injected into the column, thereby changing the material's chromatographic characteristics whereby to permit chromatographic separations that might otherwise be impossible.

Figure 5:
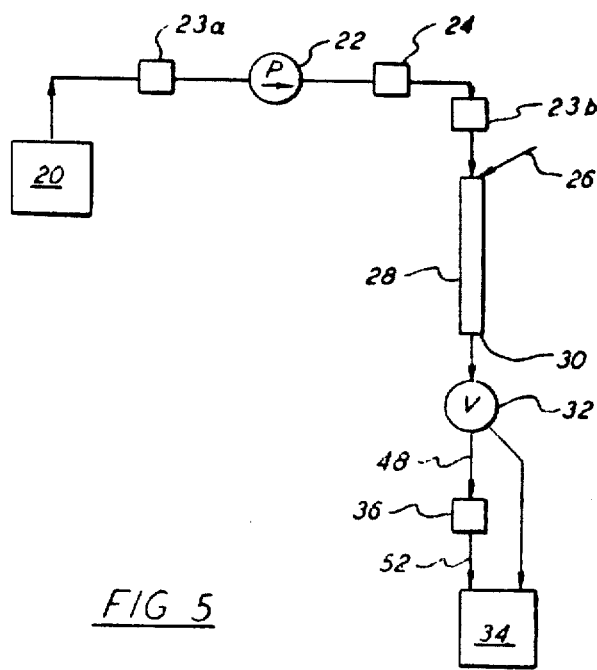
FIG. 5 is a schematic view of still another alternative form of liquid chromatography apparatus employing an amperometric guard cell in accordance with the present invention.

FIG. 5 illustrates the placement of two guard cells 23A, 23B respectively, made in accordance with the present invention, in a chromatography system, upstream and downstream of injection valve 24. This embodiment provides both screening and materials modification.

Further understanding of the principles and advantages of the present invention may be had by reference to the following examples which illustrate the use of the electrochemical detection device in accordance with the present invention.

EXAMPLE I

An ampermetric guard cell 23 made in accordance with FIGS. 2 and 3 was used. The cell comprised one active testing electrode 44 formed of graphite with 0.8μ pore size 50% porosity, two palladium oxide wire reference electrodes 50 and 52 and two palladium wire counter electrodes 46 and 48. The guard cell 23 was located in line upstream of injection valve 24, i.e. as shown in FIG. 1.

Figure 6A:
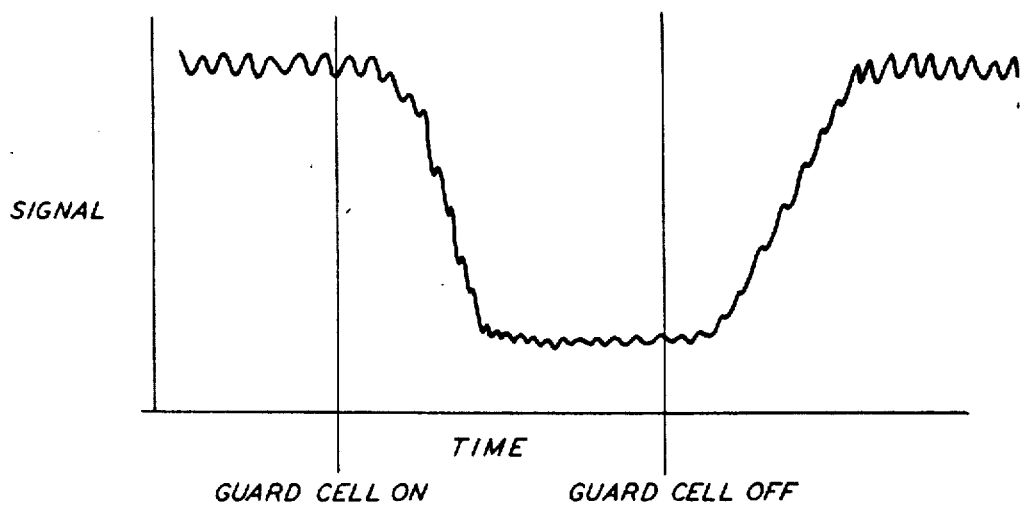
FIG. 6 is a series of chart recordings showing measurements made on the eluant from a liquid chromatography apparatus and illustrating the advantages of the present invention.

The basic procedure was to dissolve small amounts of Acetaminophen in methyl alcohol/phosphoric acid/water matrix (30% methyl alcohol, 70% water, 0.01% $H_3PO_4$) to form an eluant solution. The sample solution was then introduced into a Model 848 liquid chromatography system (available from E. I. DuPont de Nemours and Co.). The chromatography column was packed with a Zorbax- C-8 column packing from E. I. DuPont de Nemours and Co. (The manufacturer describes the packing as comprising an eight-carbon hydrocarbon on an inert carrier). Flow rate through the chromatography column was 1.5 ml/min, with an inlet pressure of 3200 psi. The eluant from the chromatography column was run through an electrochemical detection cell (Model No. 5100, available from Environmental Sciences Associates, Inc.). The electrical signal outputs from the electrochemical detection cell were recorded on an automatic recorder and shown in FIG. 6a with the guard cell 23 turned (+0.900 V.) and off. As can be seen in FIG. 6a guard cell 23 provides substantial suppression of background signals.

EXAMPLE II

Figure 6B:
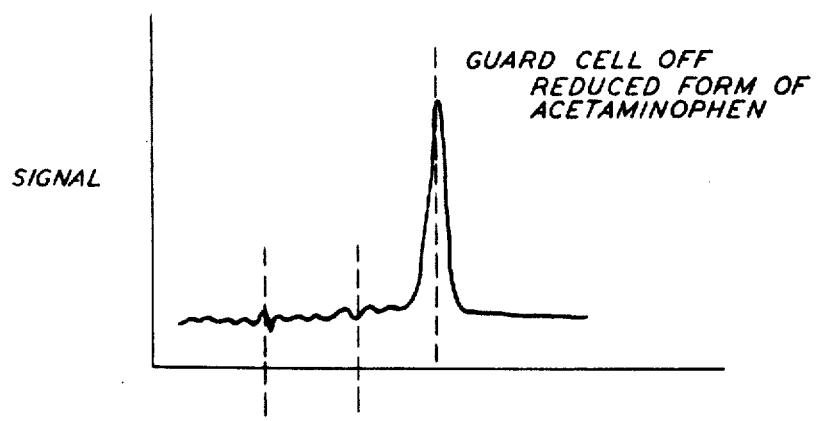
Figure 6C:
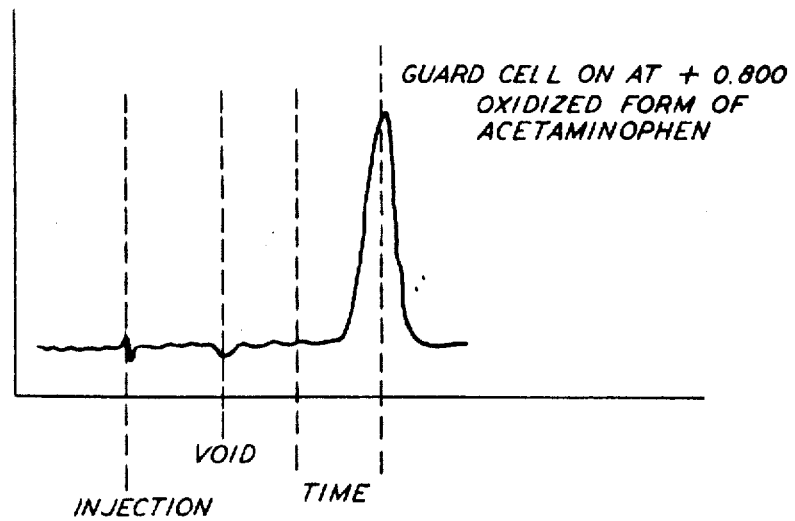

Example I was repeated with the following change: Guard cell 23 was located between injection valve 24 and chromatography column 28. The electrical signal outputs from the electrochemical detection cell 36 were recorded as before on an automatic recorder and shown in FIG. 6b and FIG. 6c with the guard cell 23 turned on (+0.800 v.) and off. As can be seen in FIG. 6b and FIG. 6c guard cell 23 provides a substantial shift in retention time for the oxidized form of Acetaminophen.

Additional cells set at other potentials may be included in line to further suppress background and/or to further modify other selected materials to change their chromatographic characteristics.

As should be clear from the foregoing the inclusion of amperometric guard cell 23 in accordance with the present invention offers a number of advantages in liquid chromatography. Furthermore, amperometric cell 23 is not limited to use as a guard cell in liquid chromatography separations, but may also be advantageously employed for monitoring or directly measuring a variety of sample solutions, for example, of industrial, enviromental, geophysical and biomedical interest. In this regard it should be noted that cell 23 is ideally suited for high pressure applications. Still other features, modifications, advantages and objects will be obvious to one skilled in the art.

I claim:

1. In a method of chromatographically analyzing a sample material wherein a sample is dissolved in a carrier fluid to form a mobile phase which then is passed through a chromatography column, electrochemically screening said carrier fluid so as to selectively remove electroactive materials therein prior to injecting said sample material into said carrier fluid by passing said carrier fluid through a flow cell having at least one active testing electrode, at least one reference electrode and at least one counter electrode, and applying controlled testing potentials to said active testing electrodes, a reference potential to said reference electrodes, and a counter potential to said counter electrodes.

2. In the method according to claim 1, comprising electrochemically oxidizing selected of said electroactive materials in said carrier fluid.

3. In the method according to claim 1, comprising electrochemically reducing selected of said electroactive materials in said carrier fluid.

4. In a method of analyzing a sample material by liquid chromatography wherein said sample is dissolved in a carrier fluid to form a mobile phase which then is passed through a chromatography column, electrochemically treating said mobile phase prior to passing said mobile phase through said chromatography column whereby to change chromatographic characteristics of selective materials therein, said electrochemical treating comprising electrochemically screening said mobile phase by passing said mobile phase through a flow cell having at least one active testing electrode, at least one reference electrode and at least one counter electrode, and applying controlled testing potentials to said active testing electrodes, a reference potential to said reference electrodes, and a counter potential to said counter electrodes.

5. In the method according to claim 4, comprising electrochemically oxidizing selected of said electroactive materials in said mobile phase.

6. In the method according to claim 4, comprising electrochemically reducing selected of said electroactive materials in said mobile phase.

7. In a method of chromatographically analyzing a sample material wherein a sample is dissolved in a carrier fluid to form a mobile phase which subsequently is passed through a chromatography column, electrochemically screening said carrier fluid so as to selectively remove electroactive materials therein prior to injecting said sample material into said carrier fluid, and electrochemically treating said mobile phase prior to passing said mobile phase through said chromatography column whereby to change chromatographic characteristics of selective materials therein.

* * * * *